United States Patent [19]

Krämer et al.

[11] 4,229,459
[45] Oct. 21, 1980

[54] COMBATING FUNGI WITH 1-AZOL-1-YL-1-PHENOXY-2-ALKANE ETHERS

[75] Inventors: Wolfgang Krämer; Karl H. Büchel, both of Wuppertal; Wilhelm Brandes, Leichlingen; Paul-Ernst Frohberger, Leverkusen; Volker Paul, Solingen, all of Fed. Rep. of Germany

[73] Assignee: Bayer Aktiengesellschaft, Leverkusen, Fed. Rep. of Germany

[21] Appl. No.: 900,401

[22] Filed: Apr. 26, 1978

[30] Foreign Application Priority Data

May 10, 1977 [DE] Fed. Rep. of Germany ....... 2720949

[51] Int. Cl.² .............. A01N 9/22; C07D 233/60; C07D 249/08
[52] U.S. Cl. .................. 424/269; 424/232; 424/245; 424/273 R; 546/347; 548/101; 548/262; 548/341
[58] Field of Search .......... 260/308 R; 548/341; 424/269, 273, 273 R

[56] References Cited

U.S. PATENT DOCUMENTS

| | | | |
|---|---|---|---|
| 3,898,341 | 8/1975 | Meiser et al. | 541/341 |
| 3,940,414 | 2/1976 | Kramer et al. | 541/341 |
| 3,952,002 | 4/1976 | Kramer et al. | 260/308 R |
| 4,036,973 | 7/1977 | Walker et al. | 548/341 |

FOREIGN PATENT DOCUMENTS 2431407 1/1976 Fed. Rep. of Germany ...... 260/308 R
2547953 4/1977 Fed. Rep. of Germany ...... 260/308 R

*Primary Examiner*—Alton D. Rollins
*Attorney, Agent, or Firm*—Sprung, Felfe, Horn, Lynch & Kramer

[57] ABSTRACT

Azolyl ether derivatives of the formula

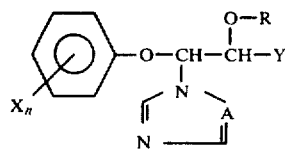

in which
 A is CH or a nitrogen atom,
 R is alkyl, alkenyl, alkynyl, phenyl, benzyl or substituted phenyl or benzyl,
 X is halogen, alkyl, alkoxy, alkylthio, alkylsulphonyl, halogenoalkyl, alkoxycarbonyl, nitro, cyano, phenyl, phenoxy, phenylthio, or substituted phenyl, phenoxy of phenylthio,
 Y is alkyl, phenyl, or substituted alkyl or phenyl and
 n is 0, 1, 2, 3, 4 or 5, which possess fungicidal properties.

7 Claims, No Drawings

COMBATING FUNGI WITH 1-AZOL-1-YL-1-PHENOXY-2-ALKANE ETHERS

The present invention relates to and has for its objects the provision of particular new azolyl ether derivatives which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has already been disclosed that certain azole derivatives, in particular 3,3-dimethyl-1-phenoxy-1-(1,2,4-triazol-1-yl)- or imidazol-1-yl-butan-2-ols and 3,3-dimethyl-1-(imidazol-1-yl)-1-phenoxy-butan-2-ones substituted in the phenyl part, and ω-(imidazol-1-yl)-ω-phenoxy-acetophenones substituted in the phenoxy part have good fungicidal properties (see U.S. Pat. Nos. 3,952,002, 3,940,414 and 3,898,341). However, their activity is not always completely satisfactory, especially when low amounts and concentrations are used.

The present invention now provides, as new compounds, the azolyl ether derivatives of the general formula

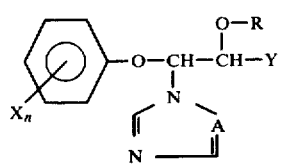

in which

A represents the CH group or a nitrogen atom,

R represents alkyl, alkenyl, alkynyl, optionally substituted phenyl or optionally substituted benzyl, X represents halogen, alkyl, alkoxy, alkylthio, alkylsulphonyl, halogenoalkyl, alkoxycarbonyl, nitro, cyano, optionally substituted phenyl, optionally substituted phenoxy or optionally substituted phenylthio, Y represents optionally substituted alkyl or optionally substituted phenyl and n represents 0, 1, 2, 3, 4 or 5, The compounds of the present invention have been found to have powerful fungicidal properties.

Preferably, R represents alkyl, alkenyl or alkynyl with up to 4 carbon atoms in each case, or represents benzyl or monosubstituted or polysubstituted benzyl, the substituents being selected from halogen (especially fluorine, chlorine or bromine), cyano, nitro, alkyl with 1 to 4 carbon atoms, alkoxycarbonyl with 1 to 4 carbon atoms in the alkyl part and halogenoalkyl with up to 2 carbon atoms and up to three halogen atoms (especially fluorine and chlorine, with trifluoromethyl being mentioned as an example of such halogenoalkyl), or represents phenyl which is optionally substituted by nitro, cyano or alkoxycarbonyl with 1 to 4 carbon atoms in the alkyl part, an additional substituent being optionally present, which is selected from halogen (especially fluorine, chlorine or bromine), alkyl with 1 to 4 carbon atoms and halogenoalkyl with up to 2 carbon atoms and up to three halogen atoms (especially fluorine and chlorine, with trifluoromethyl being mentioned as an example of such halogenoalkyl);

X represents halogen (especially fluorine, chlorine or bromine), nitro, cyano, $C_1$-$C_4$ alkyl, $C_1$-$C_4$ alkoxy, $C_1$-$C_4$ alkylthio, $C_1$-$C_4$ alkylsulphonyl, alkoxycarbonyl with 1 to 4 carbon atoms in the alkyl part, halogenoalkyl with up to 4 carbon atoms and up to 5 halogen atoms (especially with up to 2 carbon atoms and up to three identical or different halogen atoms, especially fluorine and chlorine, with trifluoromethyl being mentioned as an example of such halogenoalkyl), or optionally substituted phenyl, phenoxy or phenylthio, the substituents being selected from halogen (especially fluorine, chlorine and bromine), cyano, nitro and halogenoalkyl with up to 2 carbon atoms and up to 3 identical or different halogen atoms (especially fluorine and chlorine, with trifluoromethyl being mentioned as an example of such halogenoalkyl);

n represent 0, 1, 2 or 3; and

Y represents straight-chain or branched alkyl with 1 to 9 carbon atoms, which can optionally carry one or more substituents selected from halogen (especially chlorine or bromine), hydroxyl, cyano, the grouping —CO—OR$^1$ wherein R$^1$ represents alkyl with 1 to 4 carbon atoms, the grouping —CO—NR$^2$R$^3$ wherein R$^2$ and R$^3$ are identical or different and represent hydrogen, alkyl with 1 to 4 carbon atoms or phenyl which is optionally substituted by halogen, or the grouping —O—CO—R$^4$ wherein R$^4$ represents alkyl with 1 to 18 carbon atoms, halogenoalkyl with 1 to 4 carbon atoms and 1 to 3 halogen atoms (especially fluorine or chlorine), phenyl or benzyl, each optionally monosubstituted or polysubstituted by halogen (especially fluorine or chlorine), or cycloalkyl with 5 or 6 carbon atoms, or Y represents phenyl that is optionally monosubstituted or polysubstituted by halogen (especially fluorine, chlorine or bromine).

It is particularly preferred that Y represent tert.-butyl, 2,4-dichlorophenyl, 1,1-dimethyl-2-chloro(-bromo)-ethyl or 2-ethoxy(methoxy)-carbonyl-but-2-yl.

The compounds of the formula (I) possess two asymmetric carbon atoms; they can thus exist in the form of the two geometric isomers (erythro form and threo form), which can be obtained in varying proportions. In both cases, they exist in the form of optical isomers. The formula (I) is intended to embrace all the isomers.

Surprisingly, the azolyl ether derivatives according to the present invention have a considerably higher fungicidal activity, especially against species of powdery mildew, than the 1-azolyl-3,3-dimethyl-1-phenoxy-butan-2-ones and -ols and ω-(imidazol-1-yl)-ω-phenoxy-acetophenones, which are known from the state of the art and are the most closely related substances chemically and from the point of view of their action. The active compounds according to the invention thus represent an enrichment of the art.

The present invention also provides a process for the preparation of an azolyl ether derivative of the formula (I), in which an alcoholate of a 1-azolyl-2-hydroxy-1-phenoxy-alkane derivative, of the formula

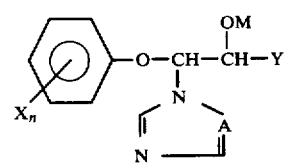

in which

A, X, Y and n have the meanings stated above and

M represents an alkali metal or a quaternary ammonium or phosphonium group, is reacted with a halide of the general formula R—Hal    (III), in which R has the meaning stated above and Hal represents chlorine or bromine, in the presence of a diluent.

In the general formula (II) M preferably represents lithium, sodium, potassium, tetrabutylammonium, N-benzyl-N,N,N-trimethylammonium, hexadecyl-trimethylammonium, 2-hydroxyethyl-trimethyl-ammonium, tetraethyl-ammonium, tetramethyl-ammonium, tetra-n-propyl-ammonium, (cyclopropylmethyl)-trimethylammonium, methyl-trioctylammonium, N-phenyl-N,N,N-trimethyl-ammonium, N-(4-methylbenzyl)-N,N,N-trimethylammonium, N,-benzyl-N,N-dimethyl-N-dodecylammonium, N,N-dibenzyl-N,N-dimethylammonium, benzyldimethyl-n-hexadecyl-ammonium, benzyldimethyl-tetradecylammonium, benzyl-tributyl-ammonium, benzyl-triethylammonium, butyl-tripropyl-ammonium, octadecyl-trimethylammonium, tetra-hexyl-ammonium, tetra-octyl-ammonium, tetra-pentyl-ammonium, tricapryl-methyl-ammonium, hexadecyl-pyridinium, tetraphenylphosphonium, hexadecyltributyl-phosphonium, ethyl-triphenyl-phosphonium or methyl-triphenyl-phosphonium.

Furthermore, the azolyl ether derivatives of the formula (I) can be used as such or in the form of salts and/or metal salt complexes, e.g. the bases can be converted into salts by reaction with acids, and the corresponding metal complexes can be obtained by reaction with metal salts.

If the sodium alcoholate of 1-(4-chlorphenoxy)-1-(1,2,4-triazol-1-yl)-3,3-dimethyl-butan-2-ol and allyl chloride are used as starting materials, the course of the reaction can be represented by the following equation

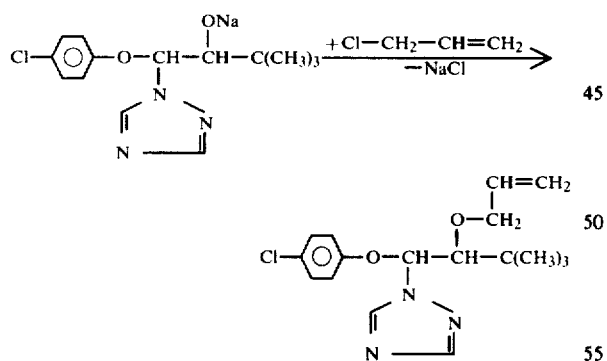

The alcoholates of the formula (II) have not hitherto been disclosed in the literature. They are obtained by reacting the corresponding 1-azolyl-2-hydroxy-1-phenoxyalkane derivatives with suitable strong bases, such as alkali metal amides or hydrides or quaternary ammonium hydroxides or phosphonium hydroxides, in an inert solvent. 1-Azolyl-2-hydroxyl-1-phenoxy-alkane derivatives are known (see U.S. Pat. Nos. 3,952,002 and 3,940,414) and are the subject of our German Patent Application Nos. P 26 32 603 of 20.7.1976, P 26 32 602 of 20.7.1976, P 26 35 663 of 7.8.1976, P 26 35 666 of 7.8.1976, 27 05 677 of 11.2.1977 and P 27 05 678 of 11.2.1977. They are obtained by reducing the corresponding azolyl-alkanone derivatives of the general formula

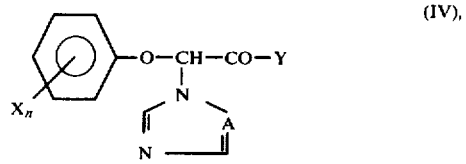

in which

A, X, Y and n have the meanings stated above, in a manner which is generally known, by means of complex hydrides, such as sodium borohydride, by means of aluminum isopropylate or by using formamidine-sulphinic acid and alkali metal hydroxide, as shown in the preparative examples hereinbelow.

Some of the compounds of the formula (IV) are also known (see U.S. Pat. Nos. 3,912,752, 4,048,318 and 3,898,341) and are the subject of the above-mentioned patents and patent applications. They are obtained by reacting halogenoketones of the general formula

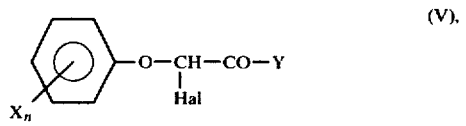

in which

X, Y and n have the meanings stated above and

Hal represents chlorine or bromine, with known azoles of the general formula

in which

A has the meaning stated above, in the presence of a diluent and an acid-binding agent, as shown in the preparative examples hereinbelow.

The halogenoketones of the formula (V) are known from the above-mentioned patents. They can be prepared, for example, by reacting known phenols of the general formula

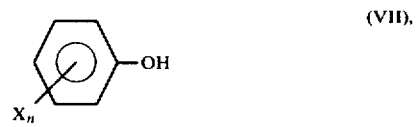

in which

X and n have the meanings stated above, with known halogenoketones of the general formula Hal—CH$_2$—CO—Y    (VIII), in which Y has the meaning stated above and Hal represents chlorine or bromine. The active hydrogen atom which still remains is then replaced by halogen in the customary manner, as shown in the preparative examples hereinbelow.

Examples of the 1-azolyl-2-hydroxy-1-phenoxyalkane derivatives from which the alcoholates of the formula (II) are derived are (azolyl representing either the 1,2,4-triazol-1-yl radical or the imidazol-1-yl radical): 1-azolyl-1-phenoxy-2-hydroxy-3,3-dimethylbutane, 1-azolyl-1-(4-chlorophenoxy)-2-hydroxy-3,3-dimethyl-butane, 1-azolyl-1-(2,4-dichlorophenoxy)-2-hydroxy-3,3-dimethyl-butane, 1-azolyl-1-(4-bromophenoxy)-2-hydroxy-3,3-dimethyl-butane, 1-azolyl-1-(4-biphenylyloxy)-2-hydroxy-3,3-dimethyl-butane, 1-azolyl-1-(4'-chloro-4-biphenylyloxy)-2-hydroxy-3,3-dimethyl-butane, 1-azolyl-1-(4-phenoxyphenoxy)-2-hydroxy-3,3-dimethyl-butane, 1-azolyl-1-(4-phenylthiophenoxy)-2-hydroxy-3,3-dimethyl-butane, 1-azolyl-1-(4'-chloro-4-phenoxyphenoxy)-2-hydroxy-3,3-dimethyl-butane, 1-azolyl-1-(4'-chloro-4-phenylthiophenoxy)-2-hydroxy-3,3-dimethyl-butane, 1-azolyl-1-(4-nitrophenoxy)-2-hydroxy-3,3-dimethyl-butane, 1-azolyl-1-(4-methoxycarbonylphenoxy)-2-hydroxy-3,3-dimethylbutane, 1-azolyl-1-(4-fluorophenoxy)-2-hydroxy-3,3-dimethyl-butane, 1-azolyl-1-(4-chlorophenoxy)-2-hydroxy-3,3-dimethyl-4-chloro-butane, 1-azolyl-1-(2,4-dichlorophenoxy)-2-hydroxy-3,3-dimethyl-4-chlorobutane, 1-azolyl-1-(4-biphenylyloxy)-2-hydroxy-3,3-dimethyl-4-chloro-butane, 1-azolyl-1-(4'-chloro-4-biphenylyloxy)-2-hydroxy-3,3-dimethyl-4-chloro-butane, 1-azolyl-1-(4'-chloro-4-phenoxyphenoxy)-2-hydroxy-3,3-dimethyl-4-chloro-butane, 1-azolyl-1-(4-nitrophenoxy)-2-hydroxy-3,3-dimethyl-4-chloro-butane, 1-azolyl-1-(4-chlorophenoxy)-2-hydroxy-3-methyl-4-acetyl-butane, 1-azolyl-1-(2,4-dichlorophenoxy)-2-hydroxy-3-methyl-4-acetyl-butane, 1-azolyl-1-(4-biphenylyloxy)-2-hydroxy-3-methyl-4-acetylbutane, 1-azolyl-1-butane, 1-azolyl-1-(4-chlorophenoxy)-2-hydroxy-3-ethoxycarbonyl-3-methyl-pentane, 1-azolyl-1-(2,4-dichlorophenoxy)-2-hydroxy-3-ethoxycarbonyl-3-methyl-pentane, 1-azolyl-1-(4-biphenylyloxy)-2-hydroxy-3-ethoxycarbonyl-3-methyl-pentane, 1-azolyl-1-(4'-chloro-4-biphenylyloxy)-2-hydroxy-3-ethoxycarbonyl-3-methyl-pentane, 1-azolyl-1-(4'-chloro-4-phenoxyphenoxy)-2-hydroxy-3-ethoxycarbonyl-3-methyl-pentane, 1-azolyl-1-(4-nitrophenoxy)-2-hydroxy-3-ethoxycarbonyl-3-methyl-pentane, 1-azolyl-1-(4-chlorophenoxy)-2-hydroxy-3-butyl-3-methoxycarbonyl-heptane, 1-azolyl-1-(2,4-dichlorophenoxy)-2-hydroxy-3-butyl-3-methoxycarbonyl-heptane, 1-azolyl-1-(4-biphenylyloxy)-2-hydroxy-3-butyl-3-methoxycarbonyl-heptane, 1-azolyl-1-(4'-chloro-4-biphenylyloxy)-2-hydroxy-3-butyl-3-methoxycarbonyl-heptane, 1-azolyl-1-(4'-chloro-4-phenoxyphenoxy)-2-hydroxy-3-butyl-3-methoxycarbonyl-heptane, 1-azolyl-1-(4-nitrophenoxy)-2-hydroxy-3-butyl-3-methoxycarbonyl-heptane, 1-azolyl-1-(4-chlorophenoxy)-2-hydroxy-2-(2,4-dichlorophenyl)-ethane, 1-azolyl-1-(2,4-dichlorophenoxy)-(4'-chloro-4-biphenylyloxy)-2-hydroxy-3-methyl-4-acetyl-butane, 1-azolyl-1-(4'-chloro-4-phenoxyphenoxy)-2-hydroxy-3-methyl-4-acetyl-butane, 1-azolyl-1-(4-nitrophenoxy)-2-hydroxy-3-methyl-4-acetyl-butane, 1-azolyl-1-(4-chlorophenoxy)-2-hydroxy-3-methyl-3-ethoxycarbonyl-butane, 1-azolyl-1-(2,4-dichlorophenoxy)-2-hydroxy-3-methyl-3-ethoxy-carbonyl-butane, 1-azolyl-1-(4-biphenylyloxy)-2-hydroxy-3-methyl-3-ethoxycarbonyl-butane, 1-azolyl-1-(4'-chloro-4-biphenylyloxy)-2-hydroxy-3-methyl-3-ethoxycarbonyl-butane, 1-azolyl-1-(4'-chloro-4-phenoxyphenoxy)-2-hydroxy-3-methyl-3-ethoxycarbonyl-butane, 1-azolyl-1-(4-nitrophenoxy)-2-hydroxy-3-methyl-3-ethoxycarbonyl-2-hydroxy-2-(2,4-dichlorophenyl)-ethane, 1-azolyl-1-(4-biphenylyloxy)-2-hydroxy-2-(2,4-dichlorophenyl)-ethane, 1-azolyl-1-(4'-chloro-4-biphenylyloxy)-2-hydroxy-2-(2,4-dichlorophenyl)-ethane, 1-azolyl-1-(4'-chloro-4-phenoxyphenoxy)-2-hydroxy-2-(2,4-dichlorophenyl)-ethane and 1-azolyl-1-(4-nitrophenoxy)-2-hydroxy-2-(2,4-dichlorophenyl)-ethane.

The starting materials of the formula (III) are generally known compounds of organic chemistry. Examples which may be mentioned are: methylene chloride, ethylene chloride, n-propyl bromide, n-butyl bromide, t-butyl bromide, allyl bromide, allyl chloride, vinyl bromide, buten-2-yl chloride, propynyl chloride, p-cyano-o-nitrochlorobenzene, p-nitrochlorobenzene, p-nitrobromobenzene, benzyl chloride, p-chlorobenzyl chloride, 2,4-dichlorobenzyl bromide, 4-nitrobenzyl chloride and 4-cyanobenzyl chloride.

Preferred salts of the compounds of the formula (I) are, for reasons of toxicity, physiologically acceptable salts, these generally being salts with physiologically acceptable acids. The preferred acids are the hydrogen halide acids (for example hydrobromic acid and especially hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The salts of the compounds of the formula (I) can be obtained in a simple manner by customary salt formation methods, for example by dissolving the base in ether, for example diethyl ether, and adding the acid, for example nitric acid, and can be isolated in a known manner, for example by filtration, and optionally purified.

The preferred metal complexes of the compounds of the formula (I) any physiologically acceptable. Preferred salts for the preparation of such complexes are those of metals of main groups II to IV and of subgroups I and II and IV to VIII, for example copper, zinc, manganese, magnesium, tin, iron and nickel. Possible anions of the salts are those which are derived from physiologically acceptable acids, preferably the hydrogen halide acids (for example hydrochloric acid), phosphoric acid, nitric acid and sulphuric acid.

The metal complexes of the compounds of the formula (I) can be obtained in a simple manner by customary processes, for example by dissolving the metal salt in alcohol, for example ethanol, and adding the solution to the compound of the formula (I). The metal salt complexes can be isolated in a known manner, for example by filtration, and optionally purified by recrystallization.

Preferred diluents which can be used for the reaction between the compound (II) and (III) are inert organic solvents, especially ethers, such as diethyl ether and dioxane;benzene; in individual cases also chlorinated hydrocarbons, such as chloroform, methylene chloride or carbon tetrachloride; and hexamethylphosphoric acid The reaction temperatures can be varied within a relatively wide range. In general, the reaction is carried out at from 20° to 150° C., preferably at the boiling point of the solvent, for example at from 60° to 100° C.

In carrying out the process according to the invention, 1 to 2 moles of the halide of the formula (III) are preferably used per mole of the alcoholate of the formula (II). In order to isolate the end products, the reaction mixture is freed from solvent, and water and an organic solvent are added to the residue. The organic phase is separated off, worked up in the customary manner and purified, and the salt is optionally prepared.

In a preferred embodiment, the procedure is to use a 1-azolyl-2-hydroxy-1-phenoxy-alkane derivative as the starting material, to convert this derivative into the alkali metal alcoholate of the formula (II) in a suitable inert organic solvent by means of an alkali metal hydride or alkali metal amide, and to react the alcoholate with a halide of the formula (III) immediately, without isolation, the compounds of the formula (I) according to the invention being obtained in one operation, with alkali metal halide being eliminated.

According to a further preferred embodiment, the preparation of the alcoholates of the formula (II) and the reaction according to the invention are carried out in a two-phase system, such as, for example, aqueous sodium hydroxide solution or potassium hydroxide solution/toluene or methylene chloride, with the addition of 0.01–1 mole of a phase transfer catalyst, such as, for example, ammonium or phosphonium compounds, the alcoholates forming in the organic phase or at the interface and being reacted with the halides present in the organic phase.

Examples of particularly active compounds according to the invention are the following: 1-(4-chlorophenoxy)-2-(2,4-dinitrophenoxy)-3,3-dimethyl-1-(1,2,4-triazol-1-yl)-butane, 2-propargyloxy-1-(4-chlorophenoxy)-3,3-dimethyl-1-(1,2,4-triazol-1-yl)-butane, 2-propargyloxy-1-(4-chlorophenoxy)-3,3-dimethyl-1-imidazol-1-yl-butane, 2-methoxy-1-(4-cyanophenoxy)-3,3-dimethyl-1-(1,2,4-triazol-1-yl)-butane, 2-methoxy-1-(4-methoxy-carbonylphenoxy)-3,3-dimethyl-1-(1,2,4-triazol-1-yl)-butane, 2-methoxy-1-(3-trifluoromethylphenoxy)-3,3-dimethyl-1-(1,2,4-triazol-1-yl)-butane, 2-ethoxy-1-(4-nitrophenoxy)-3,3-dimethyl-1-(1,2,4-triazol-1-yl)-pentane, 2-methoxy-1-(2,4-dichlorophenoxy)-3,3-dimethyl-1-imidazol-1-yl-butane, 2-ethoxy-1-(4-chloro-2-methyl-phenoxy)-3,3-dimethyl-1-(1,2,4-triazol-1-yl)-butane, 2-ethoxy-1-(4-chlorophenoxy)-3-methyl-3-ethoxycarbonyl-1-(1,2,4-triazol-1-yl)-pentane, 2-allyloxy-1-(4-chlorophenoxy)-3-methyl-3-ethoxycarbonyl-1-imidazol-1-yl-pentane, 2-methoxy-1-(4-chlorophenoxy)-3-butyl-3-methoxycarbonyl-1-imidazol-1-yl-heptane, 2-(2,4-dichlorobenzyloxy)-1-(4-chlorophenoxy)-3-methyl-3-methoxycarbonyl-1-(1,2,4-triazol-1-yl)-hexane, 2-(4-chlorobenzyloxy)-1-(4-chlorophenoxy)-3-benzyl-3-methoxycarbonyl-1-(1,2,4-triazol-1-yl)-heptane, 2-methoxy-1-(4-chlorophenoxy)-3-methyl-3-chloromethyl-1-(1,2,4-triazol-1-yl)-butane, 2-ethoxy-1-(4-chlorophenoxy)-3-methyl-3-chloromethyl-1-imidazol-1-yl-butane, 2-ethoxy-1-(4-chlorophenoxy)-3-methyl-3-bormomethyl-1-(1,2,4-triazol-1-yl)-butane, 2-alkoxy-1-(4-chlorophenoxy)-3,3-dichloromethyl-1-(1,2,4-triazol-1-yl)-butane, 2-ethoxy-1-(4-chlorophenoxy)-3,3-dimethyl-4-acetoxy-1-(1,2,4-triazol-1-yl)-butane and 2-allyloxy-1-(4-chlorophenoxy)-3,3-dimethyl-4-hydroxy-1-(1,2,4-triazol-1-yl)-butane.

Further active compounds are mentioned in the preparative examples hereinbelow.

The active compounds according to the invention exhibit a powerful fungitoxic action, and a bacteriotoxic action. They do not damage crop plants in the concentrations required for combating fungi and bacteria. For these reasons, they are suitable for use as plant protection agents for combating fungi and bacteria. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens.

They display a particularly good activity against parasitic fungi on above-ground parts of plants, such as species of Erysiphe, species of Podosphaera and species of Venturia, and also against species of Pyricularia and species of Pellicularia. Good actions are achieved against the pathogens of apple scab (*Fusicladium dendriticum*), of powdery mildew of apples (*Podosphaera leucotricha*), of powdery mildew of cucumbers (*Erysiphe cichoracearum*) and against the fungi *Pyricularia oryzae* and *Pellicularia sasakii*. Furthermore, they exhibit a high activity against cereal diseases, such as against powdery mildew of cereals, cereal rust and powdery mildew of barley.

A fact to be singled out is that the active compounds according to the invention not only display a protective action but are also systemically active. Thus it proves possible to protect plants against fungal attack by supplying the active compound to the above-ground parts of the plant through the soil and the root or through the seed.

As plant protection agents, the compounds according to the invention can be used for the treatment of soil, for the treatment of seed and for the treatment of above-ground parts of plants.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

The active compounds according to the invention can be present in the formulations as a mixture with other active compounds, such as fungicides, insecticides, acaricides, nematicides, herbicides, bird repellants, growth factors, plant nutrients and agents for improving soil structure.

The formulations in general contain from 0.1 to 95 percent by weight of active compound, preferably from 0.5 to 90 percent.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomising, dusting, scattering, dry dressing, moist dressing, wet dressing, slurry dressing or encrusting.

Especially when used as leaf fungicides, the active compound concentrations in the use forms can be varied within a fairly wide range. They are, in general, from 0.1 to 0.00001 percent by weight, preferably from 0.05 to 0.0001 percent.

In the treatment of seed, amounts of active compound of 0.001 to 50 g, preferably 0.01 to 10 g, are generally employed per kilogram of seed.

For the treatment of soil, amounts of active compound of 1 to 1,000 g, especially 10 to 200 g, are generally employed per cubic meter of soil.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative examples:

EXAMPLE 1

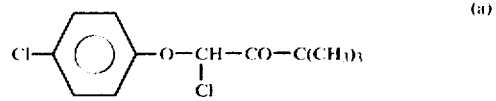

(a)

771 g (6 mols) of 4-chlorophenol were dissolved in 3,600 ml of acetone. 3 g of anhydrous sodium iodide and 910 g (6.6 mols) of anhydrous, powdered potassium carbonate were introduced and 895 g (6.3 mols) of 94.6% pure monochloropinacoline were added dropwise under reflux. After stirring the mixture at the reflux temperature for 20 hours, the precipitate was filtered off, washed with acetone and discarded. The filtrate was freed from solvent under a waterpump vacuum. The resulting white residue was taken up in 3,000 ml of carbon tetrachloride and the carbon tetrachloride solution was warmed to 60° C. 891 g (6.6 mols) of sulphuryl chloride were added dropwise to this solution, without further warming, in a manner such that gas was continuously evolved. After the addition had ended, the mixture was heated under reflux for 15 hours. Finally, the solvent was distilled off under a waterpump vacuum. 1,565 g of 1-(4-chlorophenoxy)-1-chloro-3,3-dimethylbutan-2-one were obtained in quantitative yield and could be used in further reaction without further purification.

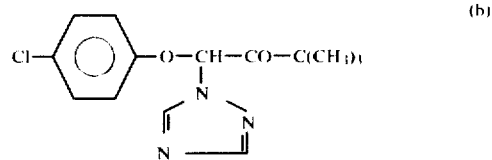

(b)

418 g (6.6 mols) of 1,2,4-triazole were dissolved in 3,000 ml of acetone. 934 g (7.2 mols) of anhydrous, powdered potassium carbonate were added to this solution, the suspension was heated to the boil and a solution of 1,565 g (6 mols) of 1-(4-chlorophenoxy)-1-chloro-3,3-dimethyl-butan-2-one in 1,500 ml of acetone was added dropwise in a manner such that the mixture boiled under reflux without heating. After the addition had ended, the mixture was heated under reflux for 15 hours in order to bring the reaction to completion; the resulting precipitate was then filtered off, washed with acetone and discarded. The filtrate was freed from solvent under a waterpump vacuum, the residue was taken up in 3,000 ml of toluene and the toluene solution was washed once with a solution of 100 g of 37% strength hydrochloric acid in 2,000 ml of water. The aqueous phase was separated off and discarded; the organic phase was washed with 5,000 ml of water and, after adding a further 4,000 ml of toluene, was stirred with a solution of 145 g of sodium hydroxide in 3,500 ml of water at room temperature for 6 hours. Thereafter, the organic phase was separated off, washed with water until neutral and freed from solvent under a waterpump vacuum. 1,535 g (87% of theory) of 1-(4-chlorophenoxy)-3,3-dimethyl-1-(1,2,4-triazol-1-yl)-butan-2-one of melting point 75°–76° C. were obtained.

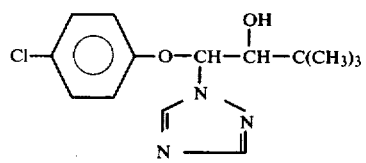

(c)

587 g (2 mols) of 1-(4-chlorophenoxy)-3,3-dimethyl-1-(1,2,4-triazol-1-yl)-butan-2-one were dissolved in 3 liters of methanol. A total of 80 g (2 mols) of sodium borohydride was added, in portions of 5 g each, to this solution at 0° to 10° C., while stirring and cooling with ice, and the mixture was stirred at 5° to 10° C. for 2 hours and then at room temperature for 12 hours. It was then cooled to 10° C. and 300 g (3 mols) of concentrated aqueous hydrochloric acid were added at 10° to 20° C. After stirring at room temperature for six hours, the resulting suspension was diluted with 3.8 liters of water which contained 400 g (4.8 mols) of sodium bicarbonate. The precipitate thereby formed was filtered off. 502 g (85% of theory) of 1-(4-chlorophenoxy)-3,3-dimethyl-1-(1,2,4-triazol-1-yl)-butan-2-ol of melting point 112°–117° C. were obtained.

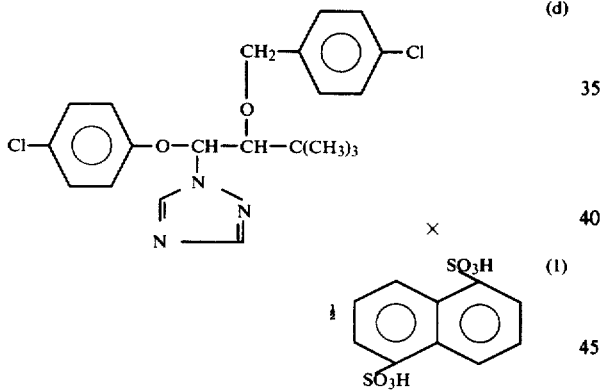

A mixture of 900 ml of 33% strength sodium hydroxide solution, 75 ml of a 50% strength solution of a butyl-dimethyldodecyl-ammonium salt and 242 g (1.5 mols) of p-chlorobenzyl chloride was added dropwise to 222 g (0.75 mol) of 1-(4-chlorophenoxy)-3,3-dimethyl-1-(1,2,4-triazol-1-yl)-butan-2-ol in 700 ml of toluene. The mixture was stirred at 80° C. for 16 hours. After cooling, the organic phase was separated off, washed with 2 liters of 5% strength hydrochloric acid, dried over sodium sulphate and concentrated by distilling off the solvent in vacuo. The oil which remained was taken up in 1.2 liters of acetone, and a solution of 100 g of 1,5-naphthalenedisulphonic acid in 500 ml of acetone was added. The crystalline precipitate was filtered off, washed with 1,000 ml of acetone and dried at 50° C. over phosphorus pentoxide in vacuo. 280 g (66% of theory) of 2-(4-chlorobenzyloxy)-1-(4-chlorophenoxy)-3,3-dimethyl-1-(1,2,4-triazol-1-yl)-butane naphthalene-1,5-disulphonate of melting point 190° C. were obtained.

EXAMPLE 2

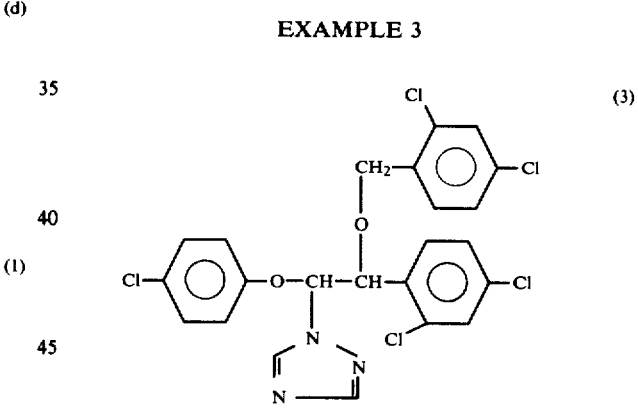

34 g (0.1 mol) of 1-(4-bromophenoxy)-3,3-dimethyl-1-(1,2,4-triazol-1-yl)-butan-2-ol were suspended in 175 ml of dioxane and the suspension was added dropwise to a mixture of 3.5 g of 80% strength sodium hydride and 125 ml of dioxane while stirring. Thereafter, the mixture was heated under reflux for one hour. After cooling, 14.5 g (0.12 mol) of allyl bromide were added dropwise at room temperature to the sodium salt thus obtained. The mixture was then heated under reflux for 15 hours, allowed to cool and concentrated by distilling off the solvent. The oily residue was taken up in 600 ml of methylene chloride and the methylene chloride solution was washed twice with 1,000 ml of water each time, dried over sodium sulphate and concentrated. The residue was distilled under a high vacuum. 30 g (79% of theory) of 2-allyloxy-1-(4-bromophenoxy)-3,3-dimethyl-1-(1,2,4-triazol-1-yl)-butane of boiling point 152°–154° C./0.2 mm Hg were obtained.

EXAMPLE 3

(3)

19.2 g (0.05 mol) of 1-(4-chlorophenoxy)-2-(2,4-dichlorophenyl)-1-(1,2,4-triazol-1-yl)-ethan-2-ol were dissolved in 100 ml of dioxane and the solution was added dropwise to a mixture of 2 g of 80% strength sodium hydride in 100 ml of dioxane at 80° C. After the evolution of hydrogen had subsided, 10 g (0.05 mol) of 2,4-dichlorobenzyl chloride were added dropwise and the mixture was heated under reflux for 15 hours. After cooling, the solvent was distilled off in vacuo and the residue was taken up in 100 ml of water and 100 ml of methylene chloride. The organic phase was separated off, washed twice with 100 ml of water each time, dried over sodium sulphate and concentrated by distilling off the solvent in vacuo. The solid residue was recrystallized from ether. 9 g (31% of theory) of 1-(4-chlorophenoxy)-2-(2,4-dichlorobenzyloxy)-2-(2,4-dichlorophenyl)-1-(1,2,4-triazol-1-yl)-ethane of melting point 132°–135° C. were obtained.

EXAMPLE 4

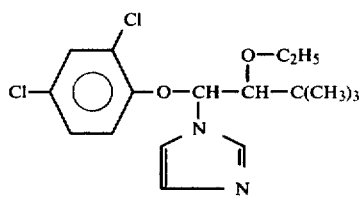
(4)

33 g (0.1 mol) of 1-(2,4-dichlorophenoxy)-3,3-dimethyl-1-imidazol-1-yl-butan-2-ol were dissolved in 150 ml of dioxane and the solution was added dropwise to 3.5 g of 80% strength sodium hydride in 150 ml of dioxane. The mixture was stirred for 3 hours at room temperature. After addition of 13.1 g (0.12 mol) of ethyl bromide, the mixture was stirred under reflux for further 17 hours. After cooling, the solvent was distilled off in vacuo, the residue was taken up in 600 ml of methylene chloride and the methylene chloride solution was washed twice with 1,000 ml of water each time, dried over sodium sulphate and distilled under a high vacuum. 10 g (28% of theory) of 2-ethoxy-1-(2,4-dichlorophenoxy)-3,3-dimethyl-1-imidazol-1-yl-butane of boiling point 170°–175° C./0.2 mm Hg were obtained.

The following compounds in Table 1 were obtained analogously:

TABLE 1 (I)

| Compound | A | R | $X_n$ | Y | Melting point (°C.) or boiling point (°C./mm Hg) |
|---|---|---|---|---|---|
| 5 | N | —CH$_2$—CH=CH$_2$ | 4-Cl | C(CH$_3$)$_3$ | 140–45 (× HCl) |
| 6 | N | —CH$_2$—CH=CH$_2$ | 4-Cl | Cl—⟨phenyl⟩—Cl | 164–66 (× HCl) |
| 7 | N | —CH$_2$—⟨2,6-Cl$_2$-phenyl⟩ | 4-⟨phenyl⟩—Cl | C(CH$_3$)$_3$ | 137–45 |
| 8 | N | —CH$_2$—⟨3,4-Cl$_2$-phenyl⟩ | 4-⟨phenyl⟩ | C(CH$_3$)$_3$ | 96 |
| 9 | N | CH$_3$ | 4-Cl | C(CH$_3$)$_3$ | viscous oil |
| 10 | N | C$_2$H$_5$ | 4-⟨phenyl⟩ | C(CH$_3$)$_3$ | viscous oil |
| 11 | N | C$_2$H$_5$ | 2,4-Cl$_2$ | C(CH$_3$)$_3$ | 145–58/0.2 |
| 12 | N | —CH$_2$—CH=CH$_2$ | 2,4-Cl$_2$ | C(CH$_3$)$_3$ | 169–74/0.2 |
| 13 | N | C$_2$H$_5$ | 4-Cl | C(CH$_3$)$_3$ | viscous oil |
| 14 | N | —CH$_2$—⟨2,6-Cl$_2$-phenyl⟩ | 2,4-Cl$_2$ | C(CH$_3$)$_3$ | 285 (× ½ NDS) |
| 15 | N | C$_2$H$_5$ | 4-⟨phenyl⟩—Cl | C(CH$_3$)$_3$ | viscous oil |
| 16 | N | —CH$_2$—CH=CH$_2$ | 4-⟨phenyl⟩—Cl | C(CH$_3$)$_3$ | 89–91 |
| 17 | N | —CH$_2$—⟨phenyl⟩—Cl | 4-⟨phenyl⟩—Cl | C(CH$_3$)$_3$ | 152 (× HCl) |
| 18 | N | —CH$_2$—CH=CH$_2$ | 4-⟨phenyl⟩ | C(CH$_3$)$_3$ | 197/0.2 |
| 19 | N | —CH$_2$—⟨phenyl⟩—Cl | 4-⟨phenyl⟩ | C(CH$_3$)$_3$ | 134–38 (× HCl) |
| 20 | N | —CH$_2$—⟨3,4-Cl$_2$-phenyl⟩ | 4-⟨phenyl⟩—Cl | C(CH$_3$)$_3$ | 154–57 |
| 21 | N | CH$_3$ | 2,4-Cl$_2$ | C(CH$_3$)$_3$ | viscous oil |
| 22 | N | C$_2$H$_5$ | 4-Br | C(CH$_3$)$_3$ | 154–58/0.2 |
| 23 | N | —CH$_2$—⟨phenyl⟩—Cl | 4-Br | C(CH$_3$)$_3$ | 175–77 (× ½ NDS) |

TABLE 1-continued $$\underset{X_n}{\text{(phenyl)}}-O-CH-\underset{\underset{N=\!\!=\!\!}{N}}{\overset{O-R}{\underset{|}{CH}}}-Y \quad (I)$$

| Compound | A | R | $X_n$ | Y | Melting point (°C.) or boiling point (°C./mm Hg) |
|---|---|---|---|---|---|
| 24 | N | —CH$_2$—(2,4-Cl$_2$-phenyl) | 4-Br | C(CH$_3$)$_3$ | 176–79 (× ½ NDS) |
| 25 | N | CH$_3$ | 4-phenyl | C(CH$_3$)$_3$ | 119–21 (A-Form) |
| 26 | N | CH$_3$ | 4-phenyl | C(CH$_3$)$_3$ | 96 (B-form) |
| 27 | N | —CH$_2$—(2,6-Cl$_2$-phenyl) | 4-Br | C(CH$_3$)$_3$ | 192–98 (× ½ NDS) |
| 28 | N | CH$_3$ | 4-(4-Cl-phenyl) | C(CH$_3$)$_3$ | 180–86 (× ½ NDS) |
| 29 | N | CH$_3$ | 4-Br | C(CH$_3$)$_3$ | 155–58/0.2 |
| 30 | N | —CH$_2$—(2,6-Cl$_2$-phenyl) | 4-phenyl | C(CH$_3$)$_3$ | 132–42 (× ½ HCl) |
| 31 | N | —CH$_2$—(4-Cl-phenyl) | 2,4-Cl$_2$ | C(CH$_3$)$_3$ | 194–96 (× ½ NDS) |
| 32 | N | —CH$_2$—(2,4-Cl$_2$-phenyl) | 4-Cl | C(CH$_3$)$_3$ | 190 (× ½ NDS) |
| 33 | N | —CH$_2$—(2,6-Cl$_2$-phenyl) | 4-Cl | C(CH$_3$)$_3$ | 116 |
| 34 | CH | —CH$_2$—(2,6-Cl$_2$-phenyl) | 4-Cl | C(CH$_3$)$_3$ | 197–205 (× HCl) |
| 35 | CH | —CH$_2$—(2,4-Cl$_2$-phenyl) | 4-Cl | C(CH$_3$)$_3$ | 213–15 (× HCl) |
| 36 | CH | CH$_3$ | 4-Cl | C(CH$_3$)$_3$ | viscous oil |
| 37 | CH | C$_2$H$_5$ | 4-Cl | C(CH$_3$)$_3$ | viscous oil |
| 38 | CH | C$_2$H$_5$ | 4-Br | C(CH$_3$)$_3$ | 166–68/0.2 |
| 39 | CH | —CH$_2$—CH=CH$_2$ | 4-Br | C(CH$_3$)$_3$ | 170–73/0.2 |
| 40 | CH | —CH$_2$—CH=CH$_2$ | 4-Cl | C(CH$_3$)$_3$ | 164–66/0.2 |
| 41 | CH | —CH$_2$—(4-Cl-phenyl) | 4-Cl | C(CH$_3$)$_3$ | 211–16 (× ½ NDS) |
| 42 | CH | —CH$_2$—(4-Cl-phenyl) | 4-Br | C(CH$_3$)$_3$ | 227–30 (× ½ NDS) |
| 43 | CH | —CH$_2$—CH=CH$_2$ | 2,4-Cl$_2$ | C(CH$_3$)$_3$ | 181–85 |
| 44 | CH | —CH$_2$—(2,4-Cl$_2$-phenyl) | 2,4-Cl$_2$ | C(CH$_3$)$_3$ | 210–20 (× ½ NDS) decomposition |
| 45 | CH | —CH$_2$—(4-Cl-phenyl) | 2,4-Cl$_2$ | C(CH$_3$)$_3$ | 250 (× ½ NDS) |

TABLE 1-continued $$\text{(I)}$$

Structure: phenyl ring with $X_n$ substituent, linked via $O-CH-CH-Y$ with $O-R$ on the middle CH, and N attached to middle CH connecting to a 5-membered ring with N=CH—A=CH.

| Compound | A | R | $X_n$ | Y | Melting point (°C.) or boiling point (°C./mm Hg) |
|---|---|---|---|---|---|
| 46 | CH | $-CH_2-$(2,6-Cl,Cl-phenyl) | 2,4-$Cl_2$ | $C(CH_3)_3$ | 238–42 (× ½ NDS) |
| 47 | CH | $C_2H_5$ | 4-(4-Cl-phenyl) | $C(CH_3)_3$ | 240 (× ½ NDS) (A-Form) |
| 48 | CH | $C_2H_5$ | 4-(4-Cl-phenyl) | $C(CH_3)_3$ | 246 (× ½ NDS) (B-Form) |
| 49 | CH | $-CH_2-CH=CH_2$ | 4-(4-Cl-phenyl) | $C(CH_3)_3$ | 247 (× ½ NDS) |
| 50 | CH | $-CH_2-$(2,3-Cl,Cl-phenyl) | 4-(4-Cl-phenyl) | $C(CH_3)_3$ | 174–76 (× ½ NDS) |
| 51 | CH | $-CH_2-$(4-Cl-phenyl) | 4-(4-Cl-phenyl) | $C(CH_3)_3$ | 228–32 (× ½ NDS) (A-Form) |
| 52 | CH | $-CH_2-$(4-Cl-phenyl) | 4-(4-Cl-phenyl) | $C(CH_3)_3$ | 170–73 (× ½ NDS) (B-Form) |
| 53 | CH | $-CH_2-$(2,3-Cl,Cl-phenyl) | 4-Br | $C(CH_3)_3$ | 249–50 (× ½ NDS) |
| 54 | CH | $-CH_2-$(2,4-Cl,Cl-phenyl) | 4-Br | $C(CH_3)_3$ | 212 (× HCl) |
| 55 | CH | $CH_3$ | 2,4-$Cl_2$ | $C(CH_3)_3$ | 165–68/0.2 |
| 56 | CH | $CH_3$ | 4-(4-Cl-phenyl) | $C(CH_3)_3$ | 230–32 (× ½ NDS) |
| 57 | CH | $CH_3$ | 4-Br | $C(CH_3)_3$ | 169–74/0.35 |
| 58 | N | $CH_3$ | 4-Cl | (2,4-Cl,Cl-phenyl) | 200–12 (× ½ NDS) |
| 59 | N | $C_2H_5$ | 4-Cl | (2,3-Cl,Cl-phenyl) | 162–65 (× HCl) |
| 60 | N | $CH_3$ | 2,4-$Cl_2$ | (2,4-Cl,Cl-phenyl) | 140–48 (× HCl) |
| 61 | CH | $C_2H_5$ | 4-(4-Cl-phenyl) | $C(CH_3)_3$ | 211 (× HCl) (A-Form) |
| 62 | CH | $-CH_2-CH=CH_2$ | 4-(4-Cl-phenyl) | $C(CH_3)_3$ | 200 (× HCl) (A-Form) |
| 63 | N | $-CH_2-$(2,4-Cl,Cl-phenyl) | 4-Cl | $C(CH_3)_3$ | 75–77 (A-Form) |
| 64 | N | $-CH_2-$(4-Cl-phenyl) | 4-Cl | $C(CH_3)_3$ | 84–86 (A-Form) |

TABLE 1-continued $$\text{(I)} \quad X_n\text{-}\underset{}{\phantom{X}}\text{-O-CH-CH-Y},\ \text{with O-R on middle carbon, N attached to CH forming triazole/imidazole ring with A}$$

| Compound | A | R | $X_n$ | Y | Melting point (°C.) or boiling point (°C./mm Hg) |
|---|---|---|---|---|---|
| 65 | N | CH$_3$ | 4-F | 3,4-Cl,Cl-phenyl (2,4-dichlorophenyl shown with one Cl) | 220 (× HCl) |
| 66 | CH | CH$_3$ | 4-Cl | C(CH$_3$)$_3$ | 188-92 (× HCl) |
| 67 | N | CH$_3$ | 4-Cl | C(CH$_3$)$_3$ | 63-66 (A-Form) |
| 68 | N | CH$_3$ | 4-Cl | C(CH$_3$)$_3$ | viscous oil |

NOTES
NDS = 1,5-naphthalenedisulphonic acid
A form and B form = in each case one of the two possible geometric isomers The following compounds of the general formula (I) could be prepared in a corresponding manner:

TABLE 2

| A | R | $X_n$ | Y |
|---|---|---|---|
| CH | CH$_3$ | 4-Cl | 3,4-dichlorophenyl |
| CH | C$_2$H$_5$ | 4-Cl | 3,4-dichlorophenyl |
| CH | —CH$_2$—CH=CH$_2$ | 4-Cl | 3,4-dichlorophenyl |
| CH | —CH$_2$—C≡CH | 4-Cl | 3,4-dichlorophenyl |
| CH | —CH$_2$-(3,4-dichlorophenyl) | 4-Cl | 3,4-dichlorophenyl |
| CH | CH$_3$ | 2,4-Cl$_2$ | 3,4-dichlorophenyl |
| CH | C$_2$H$_5$ | 2,4-Cl$_2$ | 3,4-dichlorophenyl |
| CH | n-C$_3$H$_7$ | 2,4-Cl$_2$ | 3,4-dichlorophenyl |
| N | —CH$_2$—C≡CH | 4-Cl | 3,4-dichlorophenyl |
| N | C$_2$H$_5$ | 2,4-Cl$_2$ | 3,4-dichlorophenyl |
| N | n-C$_3$H$_7$ | 2,4-Cl$_2$ | 3,4-dichlorophenyl |
| N | C$_2$H$_5$ | 4-F | 3,4-dichlorophenyl |
| N | —CH$_2$-(3,4-dichlorophenyl) | 4-F | 3,4-dichlorophenyl |

The fungicidal activity of the compounds of this invention is illustrated by the following comparative examples wherein the compounds according to the present invention are each identified by the number (given in brackets) from the preparative examples hereinabove.

The known comparison compounds are identified as follows:

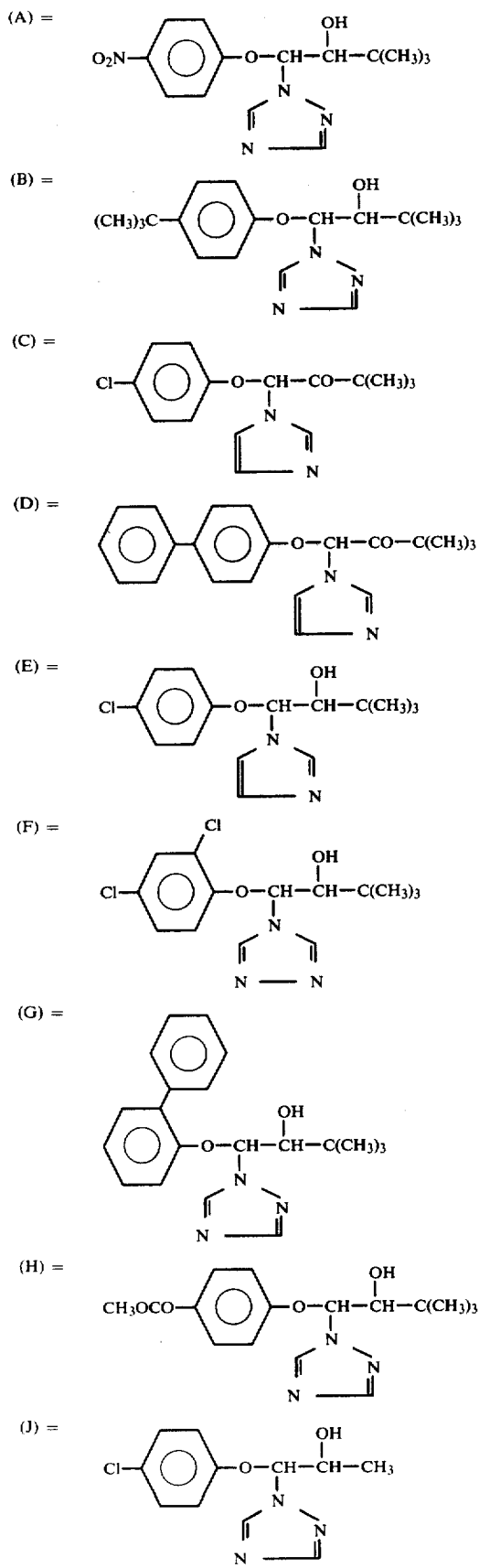
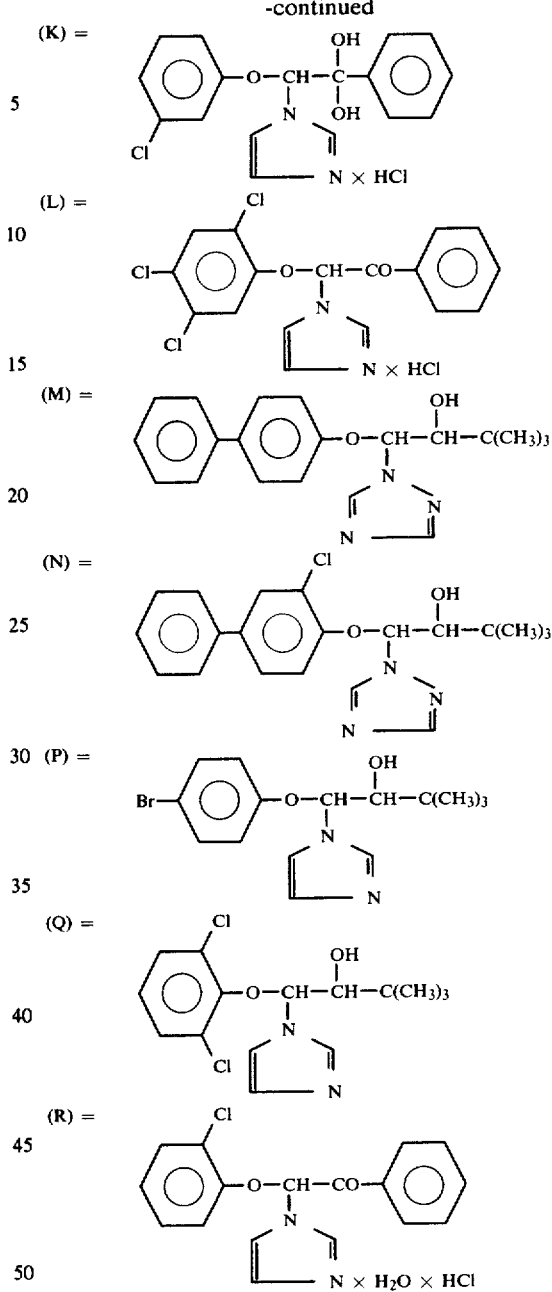

EXAMPLE 5

Podosphaera test (apple)/protective
Solvent: 4.7 parts by weight of acetone
Emulsifier: 0.3 part by weight of alkylaryl polyglycol ether
Water: 95 parts by weight.

The amount of active compound required for the desired concentration of the active compound in the spray liquid was mixed with the stated amount of solvent, and the concentrate was diluted with the stated amount of water which contained the stated amount of emulsifier.

Young apple seedlings in the 4-6 leaf stage were sprayed with the spray liquid until dripping wet. The plants remained in a greenhouse for 24 hours at 20° C.

and at a relative atmospheric humidity of 70%. They were then inoculated by dusting the conidia of the apple powdery mildew causative organism (*Podosphaera leucotricha*) and placed in a greenhouse at a temperature of 21°-23° C. and at a relative atmospheric humidity of about 70%.

10 days after the inoculation, the infection of the seedlings was determined. The assessment data were converted to % infection. 0% meant no infection; 100% meant that the plants were completely infected.

The active compounds, the concentrations of the active compounds and the results can be seen from the following table:

TABLE 3

*Podosphaera* test (apple)/protective

| Active compound | Infection in % at an active compound concentration of | | |
|---|---|---|---|
| | 0.00125% | 0.001% | 0.00062% |
| (A) | 100 | — | — |
| (B) | 100 | — | — |
| (C) | — | 100 | — |
| (D) | — | 100 | — |
| (5) | — | — | 29 |
| (32) | — | — | 0 |
| (1) | — | — | 0 |
| (9) | — | — | 0 |
| (10) | — | — | 0 |
| (11) | — | — | 7 |
| (12) | — | — | 4 |
| (13) | — | — | 1 |
| (14) | — | — | 2 |
| (15) | — | — | 2 |
| (16) | — | — | 4 |
| (19) | — | — | 55 |
| (3) | — | — | 7 |
| (6) | — | — | 0 |
| (34) | — | 50 | — |
| (36) | — | 30 | — |
| (37) | — | 57 | — |
| (38) | — | 57 | — |

EXAMPLE 6

Fusicladium test (apple)/protective
Solvent: 4.7 parts by weight of acetone
Emulsifier: 0.3 part by weight of alkylaryl polyglycol ether
Water: 95 parts by weight.

The amount of active compound required for the desired concentration of the active compound in the spray liquid was mixed with the stated amount of solvent, and the concentrate was diluted with the stated amount of water which contained the stated amount of emulsifier.

Young apple seedlings in the 4-6 leaf stage were sprayed with the spray liquid until dripping wet. The plants remained in a greenhouse for 24 hours at 20 degrees C. and at a relative atmospheric humidity of 70%. They were then inoculated with an aqueous conidium suspension of the apple scab causative organism (*Fusicladium dendriticum*) and incubated for 18 hours in a humidity chamber at 18°-20° C. and at a relative atmospheric humidity of 100%.

The plants were then brought into a greenhouse again for 14 days.

15 days after inoculation, the infection of the seedlings was determined. The assessment data were converted to percent infection. 0% meant no infection; 100% meant that the plants were totally infected.

The active compounds, the concentrations of the active compounds and the results can be seen from the following table:

TABLE 4

*Fusicladium* test (apple)/protective

| Active compound | Infection in % at an active compound concentration of 0.0025% |
|---|---|
| (E) | 83 |
| (34) | 54 |
| (36) | 40 |
| (37) | 51 |
| (38) | 40 |
| (40) | 67 |
| (42) | 65 |

EXAMPLE 7

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. hordei.

After 6 days' dwell time of the plants at a temperature of 21°-22° C. and 80-90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The active compound was the more active, the lower was the degree of mildew infection.

The active compounds, active compound concentrations in the spray liquor and degrees of infection can be seen from the table which follows:

TABLE 5

Shoot treatment test/powdery mildew of cereals/protective

| Active compounds | Active compound concentration in the spray liquor in % by weight | Infection in % of the untreated control |
|---|---|---|
| untreated | — | 100 |
| (F) | 0.01 | 26.3 |
| (G) | 0.01 | 21.3 |
| (H) | 0.01 | 37.5 |
| (J) | 0.01 | 78.8 |
| (K) | 0.01 | 66.3 |
| (L) | 0.01 | 46.3 |
| (35) | 0.0025 | 25.0 |
| (36) | 0.0025 | 0.0 |
| (37) | 0.0025 | 0.0 |
| (38) | 0.0025 | 0.0 |
| (39) | 0.0025 | 36.3 |
| (40) | 0.0025 | 0.0 |
| (33) | 0.0025 | 12.5 |
| (32) | 0.0025 | 0.0 |
| (1) | 0.0025 | 0.0 |
| (9) | 0.0025 | 0.0 |
| (10) | 0.0025 | 0.0 |
| (30) | 0.0025 | 0.0 |
| (11) | 0.0025 | 0.0 |
| (12) | 0.0025 | 0.0 |
| (13) | 0.0025 | 0.0 |

TABLE 5-continued

Shoot treatment test/powdery mildew of cereals/protective

| Active compounds | Active compound concentration in the spray liquor in % by weight | Infection in % of the untreated control |
|---|---|---|
| (14) | 0.0025 | 0.0 |
| (15) | 0.0025 | 0.0 |
| (16) | 0.0025 | 0.0 |
| (18) | 0.0025 | 0.0 |

EXAMPLE 8

Powdery mildew of barley (*Erysiphe graminis* var. hordei) (fungal disease of cereal shoots)/systemic The active compound was used as a pulverulent seed treatment agent. This was prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had developed their first leaf, they were dusted with fresh spores of *Erysiphe graminis* var. *hordei* and grown on at 21°–22° C. and 80–90% relative atmospheric humidity and 16 hours' exposure to light. The typical mildew pustules formed on the leaves over the course of 6 days.

The degree of infection was expressed as a percentage of the infection of the untreated control plants. Thus, 0% denoted no infection and 100% denoted the same degree of infection as in the case of the untreated control. The active compound was the more active, the lower was the degree of mildew infection.

The active compounds and concentrations of active compound in the seed treatment agent, as well as the amount used of the latter, and the percentage infection with mildew can be seen from the able which follows:

TABLE 6

Powdery mildew of barley test (*Erysiphe graminis* var. *hordei*)/systemic

| Active compounds | Active compound concentration in the dressing in % by weight | Amount of dressing used in g/kg of seed | Infection in % of the untreated control |
|---|---|---|---|
| no dressing | — | — | 100 |
| (M) | 25 | 10 | 100 |
| (B) | 25 | 10 | 100 |
| (N) | 25 | 10 | 100 |
| (5) | 25 | 10 | 10.0 |
| (32) | 25 | 10 | 0.0 |
| (1) | 25 | 10 | 0.0 |
| (9) | 25 | 10 | 0.0 |
| (7) | 25 | 10 | 55.0 |
| (33) | 25 | 10 | 33.8 |

EXAMPLE 9

Pellicularia test
Solvent: 11.75 parts by weight of acetone
Dispersing agent: 0.75 part by weight of alkylaryl polyglycol ether
Water: 987.50 parts by weight.

The amount of active compound required for the desired concentration of active compound in the spray liquor was mixed with the stated amount of the solvent and of the dispersing agent and the concentrate was diluted with the stated amount of water.

Rice plants about 2–4 weeks old were sprayed with the spray liquor until dripping wet. The plants remained in a greenhouse at temperatures of 22° to 24° C. and a relative atmospheric humidity of about 70% until they were dry. The plants were infected with a culture of *Pellicularia sasakii* grown on malt agar and were set up at 28° to 30° C. and 100% relative atmospheric humidity.

The infection at the leaf sheaths after 5 to 8 days was determined, in relation to the untreated but infected control. The evaluation was made on a scale from 1 to 9. 1 denoted 100% action, 3 denoted good action, 5 denoted moderate action and 9 denoted no action.

The active compounds, the concentrations of the active compounds and the results can be seen from the table which follows.

TABLE 7

*Pellicularia* test

| Active compound | Infection at an active compound concentration (in %) of 0.025 |
|---|---|
| (P) | 9 |
| (36) | 3 |
| (37) | 1 |
| (38) | 5 |

EXAMPLE 10

Mycelium growth test
Nutrient medium used:
20 parts by weight of agar-agar
200 parts by weight of potato decoction
5 parts by weight of malt
15 parts by weight of dextrose
5 parts by weight of peptone
2 parts by weight of disodium hydrogen phosphate
0.3 part by weight of calcium nitrate
Composition of the solvent mixture:
0.19 part by weight of acetone or DMF
0.01 part by weight of emulsifier (alkylaryl polyglycol ether)
1.80 parts by weight of water
Ratio of solvent mixture to nutrient medium:
2 parts by weight of solvent mixture
100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium (which had been cooled to 42° C.) and was then poured into Petri dishes of 9 cm diameter. Control plates to which the preparation had not been added were also set up.

When the nutrient medium had cooled and solidified, the plates were inoculated with the species of fungi stated in the table and incubated at about 21° C.

Evaluation was carried out after 4–10 days, dependent upon the speed of growth of the fungi. When evaluation was carried out the radial growth of the mycelium on the treated nutrient media was compared with the growth on the control nutrient medium. In the evaluation of the fungus growth, the following characteristic values were used:

1 no fungus growth
up to 3 very strong inhibition of growth
up to 5 medium inhibition of growth
up to 7 slight inhibition of growth
9 growth equal to that of untreated control.

The active compounds, the active compound concentrations and the results can be seen from the following table:

TABLE 8

| | Active compound concentration 10 ppm | Mycelium growth test | | | | | | | | |
|---|---|---|---|---|---|---|---|---|---|---|
| | | Fungi | | | | | | | | |
| Active compounds | | Fusarium culmorum | Sclerotinia sclerotiorum | Fusarium nivale | Colleto- trichum coffeanum | Cochlio- bolus miyabeanus | Botrytis cinerea | Pyricularia oryzae | Helmin- thosporium gramineum | Pellicu- laria sasakii |
| (Q) | | 9 | 9 | 9 | 9 | 9 | — | 3 | 3 | 5 |
| (R) | | 9 | 9 | 9 | 9 | 9 | 9 | 3 | 5 | — |
| (36) | | 1 | 1 | 3 | 3 | 5 | 3 | 1 | 1 | 1 |
| (37) | | 3 | 3 | 5 | — | 5 | 5 | 1 | 3 | 1 |
| (38) | | 2 | 3 | 5 | 3 | 2 | 3 | 1 | 3 | 1 |
| (39) | | 3 | 3 | 5 | 5 | 3 | 5 | 1 | 3 | 1 |
| (40) | | 3 | 3 | 3 | 5 | 3 | 5 | 1 | 2 | 1 |

It will be appreciated tht the instant specification and examples are set forth by way of illustration and not limitation, and that various modifications and changes may be made without departing from the spirit and scope of the present invention.

What we claim is:

1. A compound selected from the group consisting of 1-(4-chlorophenoxy)-2-methoxy-3,3-dimethyl-1-(1,2,4-triazol-1-yl)-butane, 1-(4-biphenylyloxy)-2-ethoxy-3,3-dimethyl-1-(1,2,4-triazol-1-yl)-butane, 1-(4-chlorophenoxy)-2-ethoxy-3,3-dimethyl-1-(1,2,4-triazol-1-yl)-butane and 1-(4-biphenylyloxy)-2-methoxy-3,3-dimethyl-1-(1,2,4-triazol-1-yl)-butane.

2. A compound according to claim 1, wherein such compound is 1-(4-chlorophenoxy)-2-methoxy-3,3-dimethyl-1-(1,2,4-triazol-1-yl)-butane of the formula

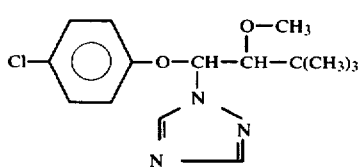

3. A compound according to claim 1, wherein such compound is 1-(4-biphenylyloxy)-2-ethoxy-3,3-dimethyl-1-(1,2,4-triazol-1-yl)-butane of the formula

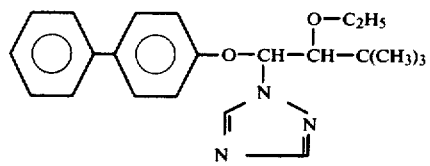

4. A compound according to claim 1, wherein such compound is 1-(4-chlorophenoxy)-2-ethoxy-3,3-dimethyl-1-(1,2,4-triazol-1-yl)-butane of the formula

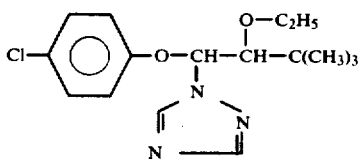

5. A compound according to claim 1, wherein such compound is 1-(4-biphenylyloxy)-2-methoxy-3,3-dimethyl-1-(1,2,4-triazol-1-yl)-butane of the formula

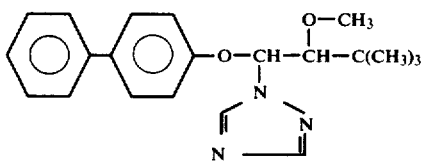

6. A fungicidal composition containing as active ingredient a fungicidally effective amount of a compound according to claim 1 in admixture with a diluent.

7. A method of combating fungi, which comprises applying to the fungi, or to a habitat thereof, fungicidally effective amount of a compound according to claim 1.

* * * * *